United States Patent [19]
D'Silva

[11] 3,966,953
[45] June 29, 1976

[54] 2-(CARBAMOYLOXIMINO)-4-THIAZOLIDINONE COMPOUNDS AS INSECTICIDAL, MITICIDAL OR NEMATOCIDAL AGENTS

[75] Inventor: Themistocles D. J. D'Silva, South Charleston, W. Va.

[73] Assignee: Union Carbide Corporation, New York, N.Y.

[22] Filed: Dec. 29, 1972

[21] Appl. No.: 319,761

[52] U.S. Cl. .......................... 424/270; 260/306.7 T; 424/DIG. 8
[51] Int. Cl.² ...................... A01N 9/12; A01N 9/20
[58] Field of Search ...................... 424/DIG. 8, 270; 260/306.7

[56] References Cited
UNITED STATES PATENTS
3,767,662  10/1973  Kay .................................. 260/306.7

FOREIGN PATENTS OR APPLICATIONS
527,558  10/1972  Switzerland

Primary Examiner—Jerome D. Goldberg
Assistant Examiner—Allen J. Robinson
Attorney, Agent, or Firm—Robert C. Brown

[57] ABSTRACT 2-(carbamoyloximino)-4-thiazolidinone compounds have been found to exhibit miticidal, nematocidal or insecticidal activity.

20 Claims, No Drawings

2-(CARBAMOYLOXIMINO)-4-THIAZOLIDINONE COMPOUNDS AS INSECTICIDAL, MITICIDAL OR NEMATOCIDAL AGENTS

This invention relates to novel 2-(carbamoyloximino)-4-thiazolidinone compositions which are useful as pesticides.

The novel compositions of this invention are the thiazolidinone carbamoyloxime compounds corresponding to the following general formula:

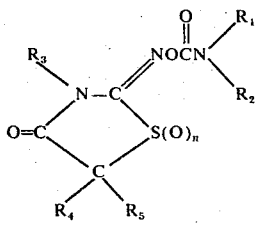

wherein $R_1$ and $R_2$ are individually, hydrogen, lower alkyl, halo-substituted lower akyl, lower alkenyl, lower alkoxyalkyl, lower alkylthioalkyl or trihalomethanesulfenyl substituents with the proviso that when $R_1$ is trihalomethanesulfenyl, $R_2$ is hydrogen or lower alkyl;

$R_3$ is hydrogen, lower alkyl, halo-substituted lower alkyl, lower alkenyl, lower dialkylamino, lower alkoxyalkyl or lower alkylthioalkyl;

$R_4$ and $R_5$ are individually hydrogen, lower alkyl, lower alkoxyalkyl or lower alkylthioalkyl and n is 0, 1 or 2.

These compositions, with varying degrees of efficacy are useful in combating insects, mites and nematodes. In general, the compositions having the greatest degree of activity are possessed by those compounds in which the combined total number of carbon atoms in the $R_3$, $R_4$ and $R_5$ substituents does not exceed about 8 carbon atoms.

The new compositions of this invention can be prepared conveniently in accordance with the following general reaction scheme:

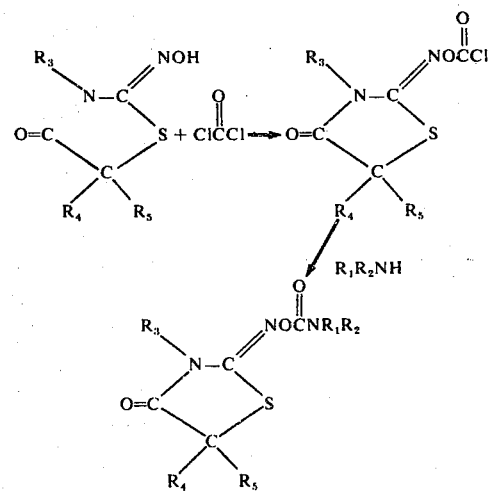

where $R_1$, $R_2$, $R_3$, $R_4$, and $R_5$ are as defined above.

The compositions of this invention where $R_1$ is hydrogen can also be prepared by reacting the appropriate oxime precursor with an isocyanate in accordance with the following general reaction scheme:

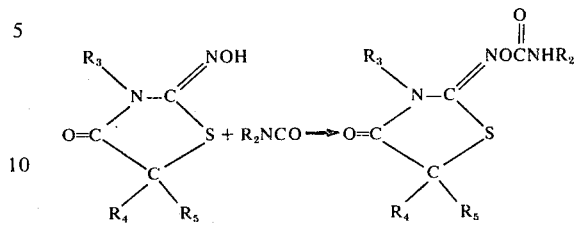

where $R_2$, $R_3$, $R_4$ and $R_5$ are as defined above.

The compositions of this invention wherein n is 1 or 2 can be prepared conveniently by selective oxidation of the corresponding thiazolidinone composition with peracetic acid.

The oxime precursor compositions are prepared by the reaction of the corresponding rhodanines with hydroxylamine hydrochloride in the presence of a mild base. (Ref. N. M. Turkevich and O. P. Milnichuk, Ukrain. Khim. Zhur., 16, 459 (1950). The rhodanine compositions can be prepared by known procedures, see for example, W. Wieniawski et. al, Roczniki Chemii, 32, 545 (1958) and references cited therein.

The following specific examples are provided to more clearly illustrate the method of preparation of the new compositions of this invention:

EXAMPLE I

PREPARATION OF 3,5,5-TRIMETHYL-2-[O-(METHYLCARBAMOYL)-OXIMINO/-4-THIAZOLIDINONE

A. 3,5,5-Trimethyl-2-oximino-4-thiazlidinone was prepared as follows: To a solution of (39.4 g) hydroxylamine hydrochloride in water was added (33.0 g) of trimethyl rhodanine in (300 ml) methanol. To this solution was added (46.3 g) sodium acetate in water and the reaction mixture was heated under reflux for 18 hours. Methanol as removed by heating under reduced pressure. The solid which precipitated out was filtered and crystallized from methanol-chloroform solution. Weight of oxime 33.1 g. m.p. 214°–217°C.

B. To a solution of 10.0 g of 3,5,5-trimethyl-2-oximino-4-thiazolidinone in 400 ml of chloroform was added 6 ml of methyl isocyanate and 3 drops of triethylamine. The reaction mixture was allowed to stand at ambient temperature for 16 hours in a pressure bottle. On concentration the residue crystallized. Recrystallized from ethyl acetate 9.5 grams of the desired product was recovered; m.p. 133°–135°C.

EXAMPLE II

SYNTHESIS OF 3-ISOPROPYL-2-[O-(METHYLCARBAMOYL) OXIMINO]-4-THIAZOLIDINONE

To a solution of 1.0 g of 3-isopropyl-2-oximino-4-thiazolidinone in 50 ml acetone-acetonitrile solution (1:1) was added 1 ml of methylisocyanate and 5 drops of triethylamine. The reaction mixture was placed in a pressure bottle and left overnight at ambient temperature. After concentrating under vacuo the residual oil was diluted with diethylether. On cooling the product crystallized. Recrystallized from ethyl ether. Weight 1.8 g. m.p. 94°–96°C.

EXAMPLE III

SYNTHESIS OF 3-ALLYL-2-[O-(METHYLCARBAMOYL) OXIMINO]-4-THIAZOLIDINONE

To a solution of (1.7 g) 3-allyl-2-oximino-4-thiazolidinone in 20 ml of acetone was added 1.0 ml methylisocyanate and 1 drop of triethylamine. The mixture was placed in a pressure bottle and left standing overnight at ambient temperature. The solution was concentrated to a solid residue. Recrystallized from ethyl acetate. Weight 1.7 g. m.p. 108°–110°C.

EXAMPLE IV

SYNTHESIS OF 3-(2-METHOXYETHYL)-2-[O-(METHYLCARBAMOYL) OXIMINO]-4-THIAZOLIDINONE

A solution of 5.4 g 3-(2-methoxyethyl)-2-oximino-4-thiazolidinone in 50 ml methylene chloride, 4.0 g of methylisocyanate and 4 drops of triethylamine was kept in a pressure bottle for 16 hours at ambient temperature. On concentration under reduced pressure the reddish brown liquid was dissolved in methanol, decolorized with charcoal and concentrated. The desired produced was crystallized from methanol. Weight 5.5 g., m.p. 153°–155°C.

EXAMPLE V

SYNTHESIS OF 3-ETHYL-2-[O-(2-CHLOROETHYLCARBAMOYL)-OXIMINO]-4-THIAZOLIDINONE

A solution of 2.0 g, 3-ethyl-2-oximino-4-thiazolidinone in 100 ml chloroform, 50 ml acetonitrile, 1.32 g., 2-chloroethylisocyanate and 2 drops of triethyl amine was placed in a pressure bottle and left standing overnight at ambient temperature. Concentration yielded 3.0 g of product. Recrystallized from isopropylether - ethyl acetate, m.p. 99°–102°C.

EXAMPLE VI

SYNTHESIS OF 3-ETHYL-2-[O-(ALLYLCARBAMOYL) OXIMINO]-4-THIAZOLIDINONE

A solution of 2.0 g of 3-ethyl-2-oximino-4-thiazolidinone in 100 ml chloroform and 50 ml of acetonitrile, 1.04 g allylisocyanate and 2 drops of triethylamine was taken in a pressure bottle and left standing overnight at ambient temperature. Concentration yielded 2.6 g of product, m.p. 103°–104°.

EXAMPLE VII

SYNTHESIS OF 3-DIMETHYLAMINO-5-METHYL-2-[O-(METHYLCARBAMOYL) OXIMINO]-4-THIAZOLIDINONE

A solution of 1.18 g of 3-dimethylamino-5-methyl-2-oximino-4-thiazolidinone in 50 ml acetone, 1.0 g methylisocyanate and 2 drops of triethylamine was placed in a pressure bottle and left standing at room temperature. After 20 hours additional 0.75 ml of methylisocyanate and 2 drops of triethylamine were added and left standing for 24 hours. Concentration yielded 5.0 g of crude product. Crystallized from methylene chloride and isopropyl ether, m.p. 110°–113°C.

EXAMPLE VIII

SYNTHESIS OF 3-ETHYL-2-[O-(METHYL-N-TRICHLOROMETHANESULFENYLCARBAMOYL) OXIMINO]-4-THIAZOLIDINONE

To a solution of 1.74 g, 3-ethyl-2-oximino-4-thiazolidinone in 25 ml of dioxane cooled to 20°C was added to a solution 2.53 g of N-methyl-N-(trichloromethanesulfenyl) carbamyl fluoride in 25 ml dioxane. To this mixture was added dropwise with external cooling 1.37 g of triethylamine. After stirring for 25 minutes the solution was diluted with 150 ml of water. The solid product was filtered off, dissolved in ethylacetate, dried and concentrated. Crystallized from acetone. Weight 2.8 g., m.p. 126°–128°C.

EXAMPLE IX

SYNTHESIS OF 3,5,5-TRIMETHYL-2-[O-(METHYLCARBAMOYL)OXIMINO]-4-THIAZOLIDINONE-1-OXIDE AND

3,5,5-TRIMETHYL-2-[O-(METHYLCARBAMOYL) OXIMINO]-4-THIAZOLIDINONE-1,1-DIOXIDE

To a solution of 1.0 g 3,5,5-trimethyl-2-[O-methylcarbamoyl] oximino-4-thiazolidinone in ethyl acetate was added about five-fold excess of peracetic acid solution in ethylacetate and the reaction mixture heated at 40°C for 8 hours. Purification by preparative thin-layer chromatography yielded the desired oxide product, m.p. 110°–112°C and the desired dioxide product, m.p. 131°–133°C.

The following compositions in addition to those described in the above Examples are illustrative of the new compositions of this invention:

2-[O-(methylcarbamoyl) oximino]-4-thiazolidinone
3-ethyl-5,5-dimethyl-2-[O-methylcarbamoyl) oximino]-4-thiazolidinone
3,5-dimethyl-2-[O-(methylcarbamoyl) oximino]-4-thiazolidinone
3-ethyl-5-methyl-2-[O-(methylcarbamoyl) oximino]-4-thiazolidinone
3-iospropyl-5-methyl-2-[O-methylcarbamoyl) oximino]-4-thiazolidinone
3-methyl-5-ethyl-2-[O-(methylcarbamoyl) oximino]-4-thiazolidinone
3,5-dimethyl-5-ethyl-2-[O-(methylcarbamoyl) oximino]-4-thiazolidinone
5,5-dimethyl-2-[O-(methylcarbamoyl) oximino]-4-thiazolidinone
3,5,5-trimethyl-2-[O-(carbamoyl) oximino]-4-thiazolidinone
3,5,5-trimethyl-2-[O-(dimethylcarbamoyl) oximino]-4-thiazolidinone
3-methyl-5,5-diethyl-2-[O-(methylcarbamoyl) oximino]-4-thiazolidinone
3,5dimethyl-5-n-propyl-2-[O-(methylcarbamoyl) oximino]-4-thiazolidinone
3,5-dimethyl-5-butyl-2-[O-(methylcarbamoyl) oximino]-4-thiazolidinone
3,5,5-triethyl-2-[O-(methylcarbamoyl) oximino]-4-thiazolidinone
3-ethyl-5-methyl-5-propyl-2-[O-(methylcarbamoyl) oximino]-4-thiazolidinone
3-ethyl-5-methyl-5-butyl-2-[O-(methylcarbamoyl) oximino]-4-thiazolidinone 3-propyl-2-[O-(methylcarbamoyl) oximino]-4-thiazolidinone
3-n-butyl-2-[O-(methylcarbamoyl) oximino]-4-thiazolidinone
3-methyl-2-[O-(methylcarbamoyl) oximino]-4-thiazolidinone
3-ethyl-2-[O-(methylcarbamoyl) oximino]-4-thiazolidinone
3-isopropyl-5,5-dimethyl-2-[O-(methylcarbamoyl) oximino]-4-thiazolidinone
3-propyl-5,5-diethyl-2-[O-(methylcarbamoyl) oximino]-4-thiazolidinone
3-propyl-5methyl-5-propyl-2-[O-(methylcarbamoyl) oximino]-4-thiazolidinone
3-propyl-5-methyl-5-butyl-2-[O-(methylcarbamoyl) oximino]-4-thiazolidinone
3,5,5-trimethyl-2-[O-(diethylcarbamoyl) oximino]-4-thiazolidinone
3-isopropyl-2-[O-(N-trichloromethanesulfenyl-N-methylcarbamoyl) oximino]-4-thiazolidinone
3-allyl-5,5-dimethyl-2-[O-methylcarbamoyl) oximino]-4-thiazolidinone
3-methallyl-5,5-dimethyl-2-[O-(methylcarbamoyl) oximino]-4-thiazolidinone
3-allyl-5-methyl-5-ethyl-2-[O-(methylcarbamoyl) oximino]-4-thiazolidinone
3,5,5-trimethyl-2-[O-(N-fluorodichloromethanesulfenyl-N-methylcarbamoyl) oximino]-4-thiazolidinone
3,5,5-trimethyl-2-[O-(N-difluorochloromethanesulfenyl-N-methylcarbamoyl) oximino]-4-thiazolidinone
3,5,5-trimethyl-2-[O-(N-trifluoromethanesulfenyl-N-methylcarbamoyl) oximino]-4-thiazolidinone
3-(3-methylthiopropyl)-5-(ethyl-2-[O-(methoxy methylcarbamoyl) oximino]-4-thiazolidinone
3,5,5-trimethyl-2-[O-(N-acetyl-N-methylcarbamoyl) oximino]-4-thiazolidinone
3,5-dimethyl-5-(2-methoxyethyl)-2-[O-(methylcarbamoyl)-oximino]-4-thiazolidinone
3-methyl-5-methylthiomethyl-2-[O-(methylcarbamoyl) oximino]-4-thiazolidinone
3-(2-methoxyethyl)-2-[O-(methylcarbamoyl) oximino]-4-thiazolidinone
3,5,5-trimethyl-1-oxo-2-[O-(methylcarbamoyl) oximino]-4-thiazolidinone
3,5,5-trimethyl-1,1-dioxo-2-[O-(methylcarbamoyl) oximino]-4-thiazolidinone Selected species of the new compounds were evaluated to determine their pesticidal activity against mites, nematodes and certain insects, including an aphid, a caterpillar, a beetle and a fly.

Suspensions of the test compound were prepared by dissolving one gram of compound in 50 milliliters of acetone in which had been dissolved 0.1 gram (10 percent of the weight of compound) of an alkylphenoxy polyethoxyethanol surfactant, as an emulsifying or dispersing agent. The resulting solution was mixed into 150 milliliters of water to give roughly 200 milliliters of a suspension containing the compound in finely divided form. The thus-prepared stock suspension contained 0.5 percent by weight of compound. The test concentrations in parts per million by weight employed in the tests described hereinbelow were obtained by appropriate dilutions of the stock suspension with water. The test procedures were as follows:

BEAN APHID FOLIAGE SPRAY TEST

Adults and nymphal stages of the bean aphid (*Aphis fabae* Scop.) reared on potted dwarf nasturtium plants at 65°–70°F. and 50–70 percent relative humidity, constituted the test insects. For testing purposes, the number of aphids per pot was standardized to 100–150 by trimming plants containing excess aphids.

The test compounds were formulated by diluting the stock suspension with water to give a suspension containing 500 parts of test compound per million parts of final formulation.

The potted plants (one pot per compound tested) infested with 100–150 aphids, were placed on a revolving turntable and sprayed with 100–110 milliliters of test compound formulation by use of a DeVilbiss spray gun set at 40 psig. air pressure. This application, which lasted 25 seconds, was sufficient to wet the plants to run-off. As a control, 100–110 milliliters of a water-acetone-emulsifier solution containing no test compound were also sprayed on infested plants. After spraying, the pots were placed on their sides on a sheet of white standard mimeograph paper which had been previously ruled to facilitate counting. Temperature and humidity in the test room during the 24 hour holding period were 65°–70°F. and 50–70 percent, respectively. Aphids which fell onto the paper and were unable to remain standing after being uprighted were considered dead. Aphids remaining on the plants were observed closely for movement and those which were unable to move the length of the body upon stimulation by prodding were considered dead. Percent mortality was recorded for various concentration levels.

SOUTHERN ARMYWORM LEAF SPRAY TEST

Larvae of the southern armyworm (*Prodenia eridania*, (Cram.)), reared on Tendergreen bean plants at a temperature of 80±5°F. and a relative humidity of 50±5 percent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulation by use of a DeVilbiss spray gun set at 10 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°–85°F. for 3 days. Although the larvae could easily consume the whole leaf within twenty-four hours, no more food was added. Larvae which were unable to move the length of the body, even upon stimulation by prodding, were considered dead. Percent mortality was recorded for various concentration levels.

MEXICAN BEAN BEETLE LEAF SPRAY TEST

Fourth instar larvae of the Mexican bean bettle (*Epilachna varivestis*, Muls.), reared on Tendergreen bean plants at a temperature of 80±5°F. and 50±5 percent relative humidity, were the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulation by use of a DeVilbiss spray gun set at 10 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80±5°F. for three days. Although the larvae could easily consume the leaf within 24 to 48 hours, no more food was added. Larvae which were unable to move the length of the body, even upon stimulation, were considered dead.

FLY BAIT TEST

Four to 6 day old adult house flies (*Musca domestica*, L.), reared according to the specifications of the Chemical Specialities Manufacturing Association (Blue Book, McNair-Dorland Co., N.Y. 1954; pages 243–244, 261) under controlled conditions of 80±5°F. and 50±5 percent relative humidity, were the test insects. The flies were immobilized by anesthetizing with carbon dioxide and twenty five immobilized individuals, males and females, were transferred to a cage consisting of a standard food strainer about five inches in diameter which was inverted over a wrapping-paper-covered surface. The test compounds were formulated by diluting the stock suspension with a 10 percent (by weight) sugar solution to give a suspension containing 500 parts of test compound per million parts of final formulation, by weight. Ten milliliters of the test formulation were added to a souffle cup containing a one-inch square of an absorbent cotton pad. This bait cup was introduced and centered on the blotting paper under the food strainer prior to admitting the anesthetized flies. The caged flies were allowed to feed on the bait for twenty four hours, at a temperature of 80±5°F. and the relative humidity of 50±5 percent. Flies which showed no sign of movement on prodding were considered dead.

MITE FOLIAGE SPRAY TEST

Adults and numphal stages of the two-spotted mite (*Tetranychus urticae* Koch), reared on Tendergreen bean plants at 80±5 percent relative humidity, were the test organisms. Infested leaves from a stock culture were placed on the primary leaves of two bean plants six to eight inches in height, growing in a two-and-a-half inch clay pot. 150–200 Mites, a sufficient number for testing, transferred from the excised leaves to the fresh plants in a period of 24 hours. Following the twenty four hour transfer period, the excised laves were removed from the infested plants. The test compounds were formulated by diluting the stock suspension with water to give a suspension containing 500 parts of test compound per million parts of final formulation. The potted plants (one pot per compound) were placed on a revolving turntable and sprayed with 100–110 milliliters of test compound formulation by use of a DeVilbiss spray gun set at 40 psig. air pressure. This application, which lasted 25 seconds, was sufficient to wet the plants to run-off. As a control, 100–110 milliliters of a water solution containing acetone and emulsifier in the same concentrations as the test compound formulation, but containing no test compound, were also sprayed on infested plants. The sprayed plants were held at 80±5 percent relative humidity for six days, after which a mortality count of motile forms was made. Microscopic examination for motile forms was made on the leaves of the test plants. Any individual which was capable of locomotion upon prodding was considered living.

NEMATOCIDE TEST

The test organism used was the infective migratory larvae of the root-knot nematode, *Meloidogyne incognita* var. acrita, reared in the greenhouse on roots of cucumber plants. Infected plants were removed from the culture, and the roots are chopped very finely. A small amount of this inoculum was added to a pint jar containing approximately 180 cc. of soil. The jars were capped and incubated for one week at room temperature. During this period eggs of the nematode were hatched, and the larval forms migrated into the soil.

Ten ml. of the test formulation were added to each of the two jars for each dosage tested. Following the addition of chemical, the jars were capped, and the contents thoroughly mixed on a ball mill for 5 minutes.

The test compounds were formulated by a standard procedure of solution in acetone addition of an emulsifier, and dilution with water. Primary screening tests were conducted at 3.33 m.g. of the test compound per jar.

The jars were left capped at room temperature for a period of 48 hours, and the contents then transferred to 3 inch pots. Subsequently, the pots were seeded to cucumber as an indicator crop and placed in the greenhouse where they were cared for in the normal fashion for approximately 3 weeks.

The cucumber plants were then taken from the pots, the soil removed from the roots, and the amount of galling visually rated.

The results of these tests are set forth in Table I below. In these tests the pesticidal activity of the compounds against aphid, mite, Southern Armyworm, Bean Beetle and house fly was rated as follows:

1 = no control
3 = partial control
5 = excellent control

In the test for activity against nematodes activity was rated as follows:

= severe galling, equal to untreated plants
2 = moderate galling
3 = light galling
4 = very light galling
5 = no galling, perfect control Dashes indicate no test conducted.

TABLE I

| Name | M.P., °C. | Aphid | Mite | Southern Armyworm | Bean Beetle | Housefly | Nematode |
|---|---|---|---|---|---|---|---|
| 2-[0-(methylcarbamoyl) oximino]-4-thiazolidinone | 148–149 | 1 | 1 | 1 | 1 | 1 | 3 |
| 3-allyl-2-[0-(methylcarbamoyl) oximino]-4-thiazolidinone | 110–112 | 1 | 5 | 5 | 5 | 5 | 3 |
| 3-n-butyl-2-[0-(methyl- carbamoyl) oximino]-4- thiazolidinone | 121–122 | 1 | 1 | 5 | 5 | 5 | 1 |
| 3-methyl-2-[0-(methyl- carbamoyl) oximino]-4- thiazolidinone | 193–195 | 1 | 1 | 1 | 3 | 5 | 1 |
| 3-ethyl-2-[0-methyl- carbamoyl) oximino]-4- thiazolidinone | 150–152 | 1 | 5 | 5 | 5 | 5 | 1 |
| 3-isopropyl-2-[0-methyl- carbamoyl) oximino]-4- thiazolidinone | 94–96 | 5 | 5 | 5 | 5 | 5 | 1 |
| 3-propyl-2-[0-methyl- carbamoyl) oximino]-4- thiazolidinone | 128–130 | 1 | 5 | 5 | 5 | 5 | 3 |
| 3,5,5-trimethyl-2-[0- (methylcarbamoyl) oximino]-4-thiazolidinone | 133–135 | 5 | 5 | 5 | 5 | 5 | 4 |
| 3-ethyl-5,5-dimethyl-2- [0-(methylcarbamoyl) oximino]-4-thiazolidinone | 105–107 | 5 | 5 | 5 | 5 | 5 | 1 |
| 3,5-dimethyl-2-[0-(methyl- carbamoyl) oximino]-4- thiazolidinone | 147–149 | 1 | 5 | 5 | 5 | 5 | 1 |
| 3-ethyl-5-methyl-2-[0-methyl- carbamoyl) oximino]-4- thiazolidinone | 134–136 | 1 | 5 | 3 | 5 | 5 | 1 |
| 3-isopropyl-5-methyl-2-[0- (methylcarbamoyl) oximino]-4- thiazolidinone | 82–83 | 5 | 5 | 5 | 5 | 5 | 2 |
| 3-methyl-5-ethyl-2-[0-(methyl- carbamoyl) oximino]-4-thiazoli- dinone | 101.5–103.5 | 1 | 3 | 5 | 5 | 5 | 1 |
| 3-(2-methoxyethyl)-5-methyl- 2-[0-(methylcarbamoyl) oximino]-4-thiazolidinone | 113–115 | 1 | 1 | 1 | 5 | 5 | 1 |
| 5,5-dimethyl-2-[0-(methyl- carbamoyl) oximino]-4- thiazolidinone | 215–218 | 1 | 1 | 1 | 5 | 5 | — |
| 3-ethyl-2-[0-(2-chloro- ethylcarbamoyl) oximino]-4- thiazolidinone | 99–102 | 1 | 3 | 1 | 1 | 5 | 1 |
| 3-ethyl-2-[0-(allylcarbamoyl) oximino]-4-thiazolidinone | 103–104 | 3 | 1 | 5 | 5 | 5 | 1 |
| 3,5,5-trimethyl-2-[0-(carbamoyl) oximino]-4-thiazolidinone | 130–132 | 1 | 3 | 1 | 5 | 5 | 1 |
| 3,5,5-trimethyl-2-[0-(dimethyl- carbamoyl) oximino]-4- thiazolidinone | 138–139 | 1 | 1 | 5 | 5 | 5 | 4 |
| 3-dimethylamino-5-methyl-2- [0-(methylcarbamoyl) oximino]- 4-thiazolidinone | 110–113 | 1 | 3 | 1 | 3 | 5 | 2 |
| 3-(2-methoxyethyl)-2-[0- methylcarbamoyl) oximino]-4- thiazolidinone | 153–155 | 3 | 5 | 5 | 5 | 5 | 1 |
| 3,5,5-trimethyl-1-oxo-2-[0- (methylcarbamoyl) oximino]-4- thiazolidinone | 110–112 | — | 1 | 1 | 3 | 5 | 1 |
| 3,5,5-trimethyl-1,1-dioxo-2- [0-(methylcarbamoyl) oximino]- 4-thiazolidinone | 131–133 | 1 | 1 | 1 | 1 | 3 | 1 |
| 5-isopropyl-2-[0-(methyl- carbamoyl) oximino]-4- thiazolidinone | 134–137 | 1 | 1 | 1 | 1 | 1 | 1 |
| 3-ethyl-2-[0-(N-(trichloro- methanesulfenyl-N-methylcarbamoyl) oximino]-4-thiazolidinone | 126–128 | 1 | 1 | 5 | 5 | 5 | 1 |
| 3-isopropyl-2-[0-(N-(trichloro- methanesulfenyl-N-methylcarbamoyl) oximino]-4-thiazolidinone | 118–119 | 1 | 5 | 5 | 5 | 5 | 2 |
| 3,5-dimethyl-5-ethyl-2-[0- (methylcarbamoyl) oximino]- 4-thiazolidinone | 78–79 | 5 | 5 | 5 | 5 | 5 | 2 |
| 3-isopropyl-5,5-dimethyl-2- [0-(methylcarbamoyl) oximino]- 4-thiazolidinone | 104–105 | 5 | 1 | 1 | 5 | 5 | — |
| 3-(2-methoxyethyl)-5,5-dimethyl- 2-[0-(methylcarbamoyl) oximino]- 4-thiazolidinone | 103–104.5° | 5 | 5 | 1 | 5 | 5 | — |
| 3-isobutyl-2-[0-(methylcarba- moyl) oximino]-4-thiazolidinone | 117–119 | 5 | 5 | 1 | 5 | 5 | — |
| 3-allyl-5,5-dimethyl-2-[0- methylcarbamoyl) oximino]-4- | 79–81 | 3 | 3 | 1 | 5 | 5 | — |

TABLE I-continued

| Name | M.P., °C. | Aphid | Mite | Southern Armyworm | Bean Beetle | Housefly | Nematode |
|---|---|---|---|---|---|---|---|
| thiazolidinone 3-(2-methoxyethoxy)propyl-2-[0-(methylcarbamoyl) oximino]-4-thiazolidinone | 76–78 | 1 | 3 | 1 | 5 | 5 | — |

At higher dosage rates all of the above compositions may be expected to exhibit some activity against the various test species, however the data presented in Table I above clearly indicates a rather high degree of selectivity for some species and a broad spectrum of activity for others.

It will be understood that the insect species employed in the above tests are merely representative of a wide variety of pests that can be controlled by use of our compounds. These compounds demonstrate systemic as well as contact toxicity against insects and mites.

It should be noted that in addition to their insecticidal and miticidal activity, noteworthy nematocidal activity was also displayed by our compounds.

The compounds contemplated in this invention may be applied as insecticides, miticides and nematocides according to methods known to those skilled in the art. Pesticidal compositions containing the compounds as the active toxicant will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytotoxic solvent such as acetone, xylene, or nitrobenzene and dispersing the toxicants in water with the acid of suiable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash it off the plant. Nonionic, anionic, or cationic dispersing and emulsifying agents may be employed, for example, the condensation products of alkylene oxides with phenol and organic acids, alkyl aryl sulfonates, complex ether alcohols, quaternary ammonium compounds, and the like.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about ¼ to 15 pounds of active toxicant per acre.

The pesticides contemplated herein prevent attack by insects, mites and nematodes upon plants or other material to which the pesticides are applied, and they have relatively high residual toxicity. With respect to plants, they have a high margin of safety in that when used in sufficient amount to kill or repel the insects, they do not burn or injure the plant, and they resist weathering which includes wash-off caused by rain, decomposition by ultra-violet light, oxidation, or hydrolysis in the presence of moisture or, at least, such decomposition, oxidation, and hydrolysis as would materially decrease the desirable pesticidal characteristic of the toxicants or impart undesirable characteristics, for instance, phytotoxicity, to the toxicants. The toxicants are so chemically inert that they are now compatible with substantially any other constituents of the spray schedule, and they may be used in the soil, upon the seeds, or the roots of plants without injuring either the seeds or roots of plants.

Experiments were also conducted to determine the phytotoxicity of representative compositions with respect to healthy fresh plants. Solutions of the compound were prepared as described above to provide a concentration of 2500 parts per million of the test compound. The test plants were sprayed in accordance with the procedure described above for the Mite Foliage Spray Test so as to deliver approximately 100 milliliters of test solution to the leaves of each plant tested. The sprayed plants and controls were set aside for approximately one hour to allow the solutions to dry and were then placed in the greenhouse. After ten days the plants were visually inspected to determine the extent of foliage injury. A rating of 1 indicates no perceptible injury; 5 indicates the plant was dead and ratings of 2, 3 and 4 indicate intermediate degrees of injury based upon the number and extent to which leaves were injured. The results of these tests are set forth in Table II below.

TABLE II

| Compound | Phytotoxicity Rating | | | |
|---|---|---|---|---|
| | Bean | Corn | Tomato | Cotton |
| 2-[0-(methylcarbamoyl) oximino]-4-thiazolidinone | 1 | 1 | 1 | 1 |
| 3-allyl-2-[0-(methylcarbamoyl) oximino]-4-thiazolidinone | 1 | 1 | 1 | 1 |
| 3-n-butyl-2-[0-(methylcarbamoyl) oximino]-4-thiazolidinone | 2 | 1 | 1 | 1 |
| 3-methyl-2-[0-(methylcarbamoyl) oximino]-4-thiazolidinone | 1 | 1 | 1 | 1 |
| 3-ethyl-2-[0-(methylcarbamoyl) oximino]-4-thiazolidinone | 1 | 1 | 1 | 1 |
| 3-isopropyl-2-[0-(methylcarbamoyl) oximino]-4-thiazolidinone | 2 | 1 | 1 | 2 |
| 3-propyl-2-[0-(methylcarbamoyl) oximino]-4-thiazolidinone | 1 | 1 | 1 | 1 |
| 3,5,5-trimethyl-2-[0-(methylcarbamoyl) oximino]-4- | | | | |

TABLE II-continued

| Compound | Phytotoxicity Rating | | | |
|---|---|---|---|---|
| | Bean | Corn | Tomato | Cotton |
| thiazolidinone | 2 | 1 | 1 | 1 |
| 3-ethyl-5,5-dimethyl-2-[0-(methylcarbamoyl) oximino]-4-thizaolidinone | 2 | 1 | 3 | 2 |
| 3,5-dimethyl-2-[0-(methylcarbamoyl) oximino]-4-thiazolidinone | 2 | 1 | 1 | 1 |
| 3-ethyl-5-methyl-2-[0-(methylcarbamoyl) oximino]-4-thiazolidinone | 2 | 1 | 2 | 1 |
| 3-isopropyl-5-methyl-2-[0-(methylcarbamoyl) oximino]-4-thiazolidinone | 2 | 1 | 2 | 1 |
| 3-methyl-5-ethyl-2-[0-(methylcarbamoyl) oximino]-4-thiazolidinone | 2 | 1 | 1 | 1 |
| 3-(2-methoxyethyl)-5-methyl-2-[0-(methylcarbamoyl) oximino]-4-thiazolidinone | 2 | 1 | 1 | 1 |
| 5,5-dimethyl-2-[0-(methylcarbamoyl) oximino]-4-thiazolidinone | 1 | 1 | 1 | 1 |
| 3-ethyl-2-[0-(2-chloroethylcarbamoyl) oximino]-4-thiazolidinone | 1 | 1 | 1 | 1 |
| 3-ethyl-2-[0-(allylcarbamoyl) oximino]-4-thiazolidinone | 1 | 1 | 1 | 1 |
| 3,5,5-trimethyl-2-[0-(carbamoyl) oximino]-4-thiazolidinone | 2 | 1 | 1 | 1 |
| 3,5,5-trimethyl-2-[0-(dimethylcarbamoyl) oximino]-4-thiazolidinone | 2 | 1 | 1 | 1 |
| 3-dimethylamino-5-methyl-2-[0-(methylcarbamoyl) oximino]-4-thiazolidinone | 2 | 1 | 2 | 1 |
| 3-(2-methoxyethyl)-2-[0-(methylcarbamoyl) oximino]-4-thiazolidinone | 1 | 1 | 1 | 1 |
| 3,5,5-trimethyl-1-oxo-2-[0-(methylcarbamoyl) oximino]-4-thiazolidinone | 1* | 1* | 1* | 1* |
| 3,5,5-trimethyl-1,1-dioxo-2-[0-(methylcarbamoyl) oximino]-4-thiazolidinone | 1 | 1 | 1 | 1 |
| 5-isopropyl-2-[0-(methylcarbamoyl) oximino]-4-thiazolidinone | 3 | 1 | 1 | 1 |
| 3-ethyl-2-[O-N-(trichloromethanesulfenyl-N-methylcarbamoyl) oximino]-4-thiazolidinone | 1 | 1 | 1 | 1 |
| 3-isopropyl-2-[0-(N-trichloromethanesulfenyl-N-methyl carbamoyl) oximino]-4-thiazolidinone | 1 | 1 | 1 | 1 |

*Composition applied at half rate

Experiments were also conducted to determine the phytoxicity of representative compounds with respect to seeds of representative plants. Seeds of rye, millett, amaranthus and mustard were used for these tests. The compounds tested were, nearly without exception, totally non-phytoxic against seeds of these plant species.

What is claimed is:

1. An insecticidal, miticidal or nematocidal composition comprising an acceptable carrier and an insecticidal, miticidal or nematocidal amount of a compound of the formula:

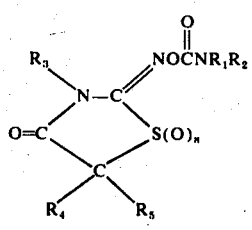

wherein:
$R_1$ is trihalomethanesulfenyl, $R_2$ is hydrogen or lower alkyl;
$R_3$ is hydrogen, lower alkyl, halo substituted lower alkyl, lower alkenyl, lower dialkylamino, lower alkoxy lower alkyl or lower alkylthio lower alkyl;
$R_4$ and $R_5$ are individually hydrogen, lower alkyl, lower alkoxy lower alkyl or lower alkylthio lower akyl; and
n is 0, 1 or 2.

2. The composition as claimed in claim 1, wherein $R_2$ is methyl and $R_1$ is trihalomethanesulfenyl.

3. The composition as claimed in claim 1 wherein $R_3$ is lower alkyl.

4. The composition as claimed in claim 1 wherein at least one of the groups $R_3$, $R_4$ and $R_5$ is lower alkyl.

5. The composition as claimed in claim 1 wherein n is 0.

6. The composition as claimed in claim 1 wherein n is 1.

7. The composition as claimed in claim 1 wherein n is 2.

8. The composition according to claim 1 wherein $R_3$, $R_4$ and $R_5$ are methyl.

9. The composition according to claim 1 wherein said compound is 3-isopropyl-2-[O-(N-trichloromethanesulfenyl-N-methylcarbamoyl)oximino]-4-thiazolidinone.

10. The composition according to claim 1 wherein said compound is 3,5,5-trimethyl-2-[O-(N-fluorodichloromethanesulfenyl-N-methylcarbamoyl)oximino]-4-thiazolidinone.

11. A method of controlling insects, mites or nematodes which comprises subjecting them to an insecticidal, miticidal or nematocidal amount of a compound of the formula:

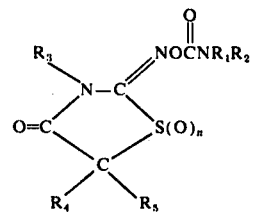

wherein:
$R_1$ is trihalomethanesulfenyl;
$R_2$ is hydrogen or lower alkyl;
$R_3$ is hydrogen, lower alkyl, halo substituted lower alkyl, lower alkenyl, lower dialkylamino, lower alkoxy lower alkyl or lower alkylthio lower akyl;
$R_4$ and $R_5$ are individually hydrogen, lower alkyl, lower alkoxy lower alkyl or lower alkylthio lower alkyl; and
n is 0, 1 or 2.

12. The method of claim 11 wherein $R_2$ is methyl and $R_1$ is trihalomethanesulfenyl.

13. The method of claim 11 wherein $R_3$ is lower alkyl.

14. The method of claim 11 wherein at least one of the groups $R_3$, $R_4$ and $R_5$ is lower alkyl.

15. The method of claim 11 wherein n is 0.

16. The method of claim 11 wherein n is 1.

17. The method of claim 11 wherein n is 2.

18. The method according to claim 11 wherein $R_3$, $R_4$, and $R_5$ are methyl.

19. The method according to claim 11 wherein said compound is 3-isopropyl-2-[O-(N-trichloromethanesulfenyl-N-methylcarbamoyl)oximino]-4-thiazolidinone.

20. The method according to claim 11 wherein said compound is 3,5,5-trimethyl-2-[O-(N-fluorodichloromethanesulfenyl-N-methylcarbamoyl)oximino]-4-thiazolidinone.

* * * * *

UNITED STATES PATENT OFFICE
CERTIFICATE OF CORRECTION

Patent No. 3,966,953          Dated June 29, 1976

Inventor(s) Themistocles D. J. D'Silva

It is certified that error appears in the above-identified patent and that said Letters Patent are hereby corrected as shown below:

Column 2, line 35 "/" should read "]".

Column 2, line 36 "thiazlidinone" should read "thiazolidinone".

Column 2, line 42 "as" should read "was".

Column 4, line 45 "iospropyl" should read "isopropyl".

Column 4, line 59 after "3,5" insert "-".

Column 7, line 55 "numphal" should read "nymphal".

Column 7, line 65 "laves" should read "leaves".

Column 8, line 61 before "=severe galling, equal to untreated plants" insert "1".

Column 11, line 37 "suiable" should read "suitable".

Column 13, lines 61 and 62 "$R_2$" should read "$R_1$" and on line 62 "$R_1$" should read "$R_2$".

Signed and Sealed this

Ninth Day of November 1976

[SEAL]

Attest:

RUTH C. MASON
Attesting Officer

C. MARSHALL DANN
Commissioner of Patents and Trademarks